United States Patent
KenKnight et al.

(10) Patent No.: US 7,392,084 B2
(45) Date of Patent: Jun. 24, 2008

(54) DEMAND-BASED CARDIAC FUNCTION THERAPY

(75) Inventors: Bruce H. KenKnight, Maple Grove, MN (US); Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 300 days.

(21) Appl. No.: 10/669,170

(22) Filed: Sep. 23, 2003

(65) Prior Publication Data

US 2005/0065554 A1    Mar. 24, 2005

(51) Int. Cl.
  *A61N 1/368* (2006.01)
(52) U.S. Cl. .............................. 607/18; 607/19; 607/23; 607/24
(58) Field of Classification Search ...................... 607/9, 607/14, 17–27, 4–6, 50; 600/513, 520, 526–527
See application file for complete search history.

(56) References Cited

U.S. PATENT DOCUMENTS

| | | | |
|---|---|---|---|
| 4,114,627 A | 9/1978 | Lewyn et al. |
| 4,777,960 A | 10/1988 | Berger et al. |
| 4,791,931 A | 12/1988 | Slate |
| 4,872,459 A | 10/1989 | Pless et al. |
| 4,880,005 A | 11/1989 | Pless et al. |
| 4,945,909 A | 8/1990 | Fearnot et al. |
| 5,014,698 A | 5/1991 | Cohen |
| 5,063,927 A | 11/1991 | Webb et al. |
| 5,111,815 A | 5/1992 | Mower |
| 5,183,040 A | 2/1993 | Nappholz et al. |
| 5,190,035 A | 3/1993 | Salo et al. |
| 5,197,467 A | 3/1993 | Steinhaus et al. |
| 5,199,428 A | 4/1993 | Obel et al. |
| 5,201,808 A | 4/1993 | Steinhaus et al. |
| 5,203,326 A | 4/1993 | Collins |

(Continued)

FOREIGN PATENT DOCUMENTS

EP    0555988 A2    8/1993

(Continued)

OTHER PUBLICATIONS

"Heart Rate Variability: Standards of Measurement, Physiological Interpretation, and Clinical Use", *European Heart Journal*, 17, Prepared by the Task Force of The European Society of Cardiology and The North American Society of Pacing and Electrophysiology; published by the American Heart Association, Inc.; European Society of Cardiology,(1996),pp. 354-381.

(Continued)

*Primary Examiner*—Carl Layno
*Assistant Examiner*—Jessica L. Reidel
(74) *Attorney, Agent, or Firm*—Schwegman, Lundberg & Woessner, P.A.

(57) ABSTRACT

A method and device for delivering cardiac function therapy on a demand basis. An implantable device for delivering cardiac function therapy is programmed to suspend such therapy at periodic intervals or upon command from an external programmer. Measurements related to hemodynamic performance are then taken using one or more sensing modalities incorporated into the device. Based upon these measurements, the device uses a decision algorithm to determine whether further delivery of the cardiac function therapy is warranted.

9 Claims, 3 Drawing Sheets

U.S. PATENT DOCUMENTS

| | | | |
|---|---|---|---|
| 5,222,493 A | 6/1993 | Sholder | |
| 5,243,980 A | 9/1993 | Mehra | |
| 5,269,301 A | 12/1993 | Cohen | |
| 5,271,395 A | 12/1993 | Wahlstrand et al. | |
| 5,273,034 A | 12/1993 | Nilsson | |
| 5,291,400 A | 3/1994 | Gilham | |
| 5,300,093 A | 4/1994 | Koestner et al. | |
| 5,303,702 A | 4/1994 | Bonnet et al. | |
| 5,318,592 A | 6/1994 | Schaldach | |
| 5,318,597 A | 6/1994 | Hauck et al. | |
| 5,324,310 A | 6/1994 | Greeninger et al. | |
| 5,330,507 A | 7/1994 | Schwartz | |
| 5,331,966 A | 7/1994 | Bennett et al. | |
| 5,341,811 A | 8/1994 | Cano | |
| 5,356,425 A | 10/1994 | Bardy et al. | |
| 5,360,436 A | 11/1994 | Alt et al. | |
| 5,391,190 A | 2/1995 | Pederson et al. | |
| 5,411,531 A | 5/1995 | Hill et al. | |
| 5,423,870 A | 6/1995 | Olive et al. | |
| 5,431,687 A | 7/1995 | Kroll | |
| 5,431,693 A | 7/1995 | Schroeppel | |
| 5,437,285 A | 8/1995 | Verrier et al. | |
| 5,441,524 A | 8/1995 | Rueter et al. | |
| 5,443,485 A | 8/1995 | Housworth et al. | |
| 5,466,245 A | 11/1995 | Spinelli et al. | |
| 5,480,412 A | 1/1996 | Mouchawar et al. | |
| 5,487,752 A * | 1/1996 | Salo et al. | 607/17 |
| 5,507,784 A | 4/1996 | Hill et al. | |
| 5,507,785 A | 4/1996 | Deno | |
| 5,522,854 A | 6/1996 | Ideker et al. | |
| 5,531,772 A | 7/1996 | Prutchi | |
| 5,560,370 A | 10/1996 | Verrier et al. | |
| 5,562,711 A | 10/1996 | Yerich et al. | |
| 5,562,712 A | 10/1996 | Steinhaus et al. | |
| 5,571,144 A | 11/1996 | Schroeppel | |
| 5,578,061 A | 11/1996 | Stroetmann et al. | |
| 5,601,615 A | 2/1997 | Markowitz et al. | |
| 5,603,331 A | 2/1997 | Heemels et al. | |
| 5,626,622 A | 5/1997 | Cooper | |
| 5,626,624 A | 5/1997 | Schaldach et al. | |
| 5,645,570 A | 7/1997 | Corbucci | |
| 5,658,318 A | 8/1997 | Stroetmann et al. | |
| 5,682,901 A | 11/1997 | Kamen | |
| 5,685,316 A | 11/1997 | Schookin et al. | |
| 5,690,681 A | 11/1997 | Geddes et al. | |
| 5,700,282 A | 12/1997 | Zabara | |
| 5,700,283 A | 12/1997 | Salo | |
| 5,718,720 A | 2/1998 | Prutchi et al. | |
| 5,722,997 A | 3/1998 | Nedungadi et al. | |
| 5,749,900 A | 5/1998 | Schroeppel et al. | |
| 5,755,671 A | 5/1998 | Albrecht et al. | |
| 5,766,225 A | 6/1998 | Kramm | |
| 5,782,884 A | 7/1998 | Stotts et al. | |
| 5,792,194 A | 8/1998 | Morra | |
| 5,817,135 A | 10/1998 | Cooper et al. | |
| 5,817,136 A | 10/1998 | Nappholz et al. | |
| 5,824,020 A | 10/1998 | Cooper | |
| 5,824,029 A | 10/1998 | Weijand et al. | |
| 5,842,997 A | 12/1998 | Verrier et al. | |
| 5,843,136 A | 12/1998 | Zhu et al. | |
| 5,861,012 A | 1/1999 | Stroebel | |
| 5,873,898 A | 2/1999 | Hemming et al. | |
| 5,891,044 A | 4/1999 | Golosarsky et al. | |
| 5,893,882 A | 4/1999 | Peterson et al. | |
| 5,916,239 A | 6/1999 | Geddes et al. | |
| 5,921,940 A | 7/1999 | Verrier et al. | |
| 5,935,081 A | 8/1999 | Kadhiresan | |
| 5,941,831 A | 8/1999 | Turcott | |
| 5,978,707 A | 11/1999 | Krig et al. | |
| 5,978,710 A | 11/1999 | Prutchi et al. | |
| 5,987,356 A | 11/1999 | DeGroot | |
| 6,006,134 A | 12/1999 | Hill et al. | |
| 6,021,351 A | 2/2000 | Kadhiresan et al. | |
| 6,022,322 A | 2/2000 | Prutchi | |
| 6,026,320 A | 2/2000 | Carlson et al. | |
| 6,035,233 A | 3/2000 | Schroeppel et al. | |
| 6,042,548 A | 3/2000 | Giuffre | |
| 6,044,294 A | 3/2000 | Mortazavi et al. | |
| 6,058,331 A | 5/2000 | King | |
| 6,073,048 A | 6/2000 | Kieval et al. | |
| 6,076,015 A | 6/2000 | Hartley et al. | |
| 6,128,535 A | 10/2000 | Maarse | |
| 6,134,470 A | 10/2000 | Hartlaub | |
| 6,135,970 A | 10/2000 | Kadhiresan et al. | |
| 6,144,878 A | 11/2000 | Schroeppel et al. | |
| 6,151,524 A | 11/2000 | Krig et al. | |
| 6,161,042 A | 12/2000 | Hartley et al. | |
| 6,167,308 A * | 12/2000 | DeGroot | 607/14 |
| 6,178,349 B1 | 1/2001 | Kieval | |
| 6,181,966 B1 | 1/2001 | Nigam | |
| 6,216,032 B1 | 4/2001 | Griffin et al. | |
| 6,224,553 B1 | 5/2001 | Nevo | |
| 6,238,422 B1 | 5/2001 | Van Oort | |
| 6,240,314 B1 | 5/2001 | Plicchi et al. | |
| 6,246,909 B1 | 6/2001 | Ekwall | |
| 6,269,263 B1 | 7/2001 | Ohnishi et al. | |
| 6,272,377 B1 | 8/2001 | Sweeney et al. | |
| 6,273,856 B1 | 8/2001 | Sun et al. | |
| 6,292,693 B1 * | 9/2001 | Darvish et al. | 607/9 |
| 6,292,695 B1 | 9/2001 | Webster, Jr. et al. | |
| 6,301,499 B1 | 10/2001 | Carlson et al. | |
| 6,317,632 B1 | 11/2001 | Krig et al. | |
| 6,358,201 B1 | 3/2002 | Childre et al. | |
| 6,370,424 B1 | 4/2002 | Prutchi | |
| 6,371,922 B1 | 4/2002 | Baumann et al. | |
| 6,390,986 B1 | 5/2002 | Curcie et al. | |
| 6,400,982 B2 | 6/2002 | Sweeney et al. | |
| 6,421,557 B1 | 7/2002 | Meyer | |
| 6,424,865 B1 * | 7/2002 | Ding | 607/9 |
| 6,438,421 B1 | 8/2002 | Stahmann et al. | |
| 6,449,507 B1 | 9/2002 | Hill et al. | |
| 6,453,201 B1 | 9/2002 | Daum et al. | |
| 6,456,880 B1 * | 9/2002 | Park et al. | 607/25 |
| 6,459,929 B1 | 10/2002 | Hopper et al. | |
| 6,463,326 B1 | 10/2002 | Hartley et al. | |
| 6,470,210 B1 | 10/2002 | Chen et al. | |
| 6,473,644 B1 | 10/2002 | Terry, Jr. et al. | |
| 6,473,647 B1 * | 10/2002 | Bradley | 607/27 |
| 6,480,733 B1 | 11/2002 | Turcott | |
| 6,480,742 B2 | 11/2002 | Stahmann et al. | |
| 6,487,450 B1 | 11/2002 | Chen et al. | |
| 6,493,585 B2 | 12/2002 | Plicchi et al. | |
| 6,511,500 B1 | 1/2003 | Rahme | |
| 6,522,914 B1 | 2/2003 | Huvelle | |
| 6,522,926 B1 | 2/2003 | Kieval et al. | |
| 6,529,772 B2 | 3/2003 | Carlson et al. | |
| 6,532,388 B1 | 3/2003 | Hill et al. | |
| 6,542,774 B2 | 4/2003 | Hill et al. | |
| 6,564,096 B2 | 5/2003 | Mest | |
| 6,571,121 B2 | 5/2003 | Schroeppel et al. | |
| 6,571,122 B2 | 5/2003 | Schroeppel et al. | |
| 6,611,713 B2 | 8/2003 | Schauerte | |
| 6,622,041 B2 | 9/2003 | Terry, Jr. et al. | |
| 6,628,987 B1 | 9/2003 | Hill et al. | |
| 6,628,988 B2 * | 9/2003 | Kramer et al. | 607/9 |
| 6,647,289 B2 | 11/2003 | Prutchi | |
| 6,690,971 B2 | 2/2004 | Schauerte et al. | |
| 6,748,261 B1 * | 6/2004 | Kroll et al. | 600/510 |
| 6,763,267 B2 | 7/2004 | Ding | |
| 6,824,538 B2 | 11/2004 | Chen | |
| 6,850,801 B2 | 2/2005 | Kieval et al. | |
| 6,856,829 B2 | 2/2005 | Ohsaki et al. | |
| 6,865,420 B1 | 3/2005 | Kroll | |
| 6,915,160 B2 * | 7/2005 | Auricchio et al. | 607/9 |

| | | | |
|---|---|---|---|
| 6,965,797 B2* | 11/2005 | Pastore et al. | 607/17 |
| 6,973,349 B2* | 12/2005 | Salo | 607/11 |
| 7,062,314 B2 | 6/2006 | Zhu et al. | |
| 7,065,405 B2* | 6/2006 | Pastore et al. | 607/9 |
| 7,069,070 B2 | 6/2006 | Carlson et al. | |
| 7,103,410 B2* | 9/2006 | Kramer et al. | 607/9 |
| 7,158,824 B2* | 1/2007 | Girouard et al. | 607/2 |
| 2002/0058877 A1 | 5/2002 | Baumann et al. | |
| 2002/0062139 A1* | 5/2002 | Ding | 607/25 |
| 2002/0107552 A1 | 8/2002 | Krig et al. | |
| 2002/0107553 A1 | 8/2002 | Hill et al. | |
| 2002/0120306 A1* | 8/2002 | Zhu et al. | 607/25 |
| 2002/0123768 A1 | 9/2002 | Gilkerson | |
| 2002/0123769 A1 | 9/2002 | Panken et al. | |
| 2002/0128563 A1 | 9/2002 | Carlson et al. | |
| 2002/0143369 A1 | 10/2002 | Hill et al. | |
| 2002/0161410 A1 | 10/2002 | Kramer et al. | |
| 2002/0165586 A1 | 11/2002 | Hill et al. | |
| 2003/0003052 A1 | 1/2003 | Hampton | |
| 2003/0004549 A1 | 1/2003 | Hill et al. | |
| 2003/0045909 A1 | 3/2003 | Gross et al. | |
| 2003/0060857 A1 | 3/2003 | Perrson et al. | |
| 2003/0069609 A1 | 4/2003 | Thompson | |
| 2003/0078623 A1 | 4/2003 | Weinberg et al. | |
| 2003/0100924 A1 | 5/2003 | Foreman et al. | |
| 2003/0105493 A1 | 6/2003 | Salo et al. | |
| 2003/0114889 A1 | 6/2003 | Huvelle et al. | |
| 2003/0135126 A1 | 7/2003 | Kuo | |
| 2003/0149450 A1 | 8/2003 | Mayberg | |
| 2003/0199956 A1* | 10/2003 | Struble et al. | 607/122 |
| 2003/0212440 A1 | 11/2003 | Boveja | |
| 2004/0093034 A1 | 5/2004 | Girouard et al. | |
| 2004/0093035 A1 | 5/2004 | Schwartz et al. | |
| 2004/0102908 A1 | 5/2004 | Larson et al. | |
| 2004/0116820 A1 | 6/2004 | Daum et al. | |
| 2004/0133247 A1 | 7/2004 | Stahmann et al. | |
| 2004/0158295 A1 | 8/2004 | Dyjach et al. | |
| 2004/0215238 A1* | 10/2004 | van Dam et al. | 607/4 |
| 2004/0220636 A1* | 11/2004 | Burnes | 607/17 |
| 2004/0230241 A1 | 11/2004 | Carlson et al. | |
| 2005/0090719 A1 | 4/2005 | Scheiner et al. | |
| 2005/0261741 A1 | 11/2005 | Libbus et al. | |
| 2006/0195038 A1 | 8/2006 | Carlson et al. | |
| 2006/0241704 A1 | 10/2006 | Shuros et al. | |
| 2006/0259088 A1 | 11/2006 | Pastore et al. | |
| 2006/0287684 A1 | 12/2006 | Baynham et al. | |

FOREIGN PATENT DOCUMENTS

| | | |
|---|---|---|
| EP | 0709058 A1 | 1/1996 |
| EP | 0709112 A2 | 5/1996 |
| EP | 1437159 A1 | 7/2004 |
| WO | WO-94/06350 A1 | 3/1994 |
| WO | WO-98/15319 A1 | 4/1998 |
| WO | WO-00/04950 A2 | 2/2000 |
| WO | WO-00/38782 A1 | 7/2000 |
| WO | WO-00/44274 A2 | 8/2000 |
| WO | WO-00/51680 A1 | 9/2000 |
| WO | WO-04033036 A2 | 4/2004 |
| WO | WO-2006079010 A1 | 7/2006 |
| WO | WO-2006121842 A3 | 11/2006 |

OTHER PUBLICATIONS

"International Search Report for corresponding PCT Application No. PCT/US2004/031062", (Feb. 17, 2005),5 pgs.

Behrens, S., "Effects of Amiodarone on the Circadian Pattern of Sudden Cardiac Death (Department of Vererans Affairs Congestive Heart Failure-Survival Trial of Antiarrhythmic Therapy)", *Am. J. Cardiol.*, 80(1), (Jul. 1997),45-48.

Behrens, S., "Modification of the Circadian Pattern of Ventricular Tachyarrhythmias by Beta-Blocker Therapy", *Clin. Cardiol.*, 20(3), (Mar. 1997),253-257.

Berger, R. D., "An Efficient Algorithm for Spectral Analysis of Heart Rate Variability", *IEEE Transactions on Biomedical Engineering, BME-33* (9), (Sep. 1986),900-904.

Bigger, J. T., "Correlations Among Time and Frequency Domain Measures of Heart Period Variability Two Weeks After Acute Myocardial Infarction", *Arrhythmias and Conduction Disturbances*, 69. (Apr. 1, 1992),891-898.

Bigger, Jr., J. T., "Spectral Analysis of R-R Variability to Evaluate Autonomic Physiology and Pharmacology and to Predict Cardiovascular Outcomes in Humans", *Am. J. Cardiol.*, 69(9), (Apr. 1, 1992),891-898.

Libbus, I. , "Combined Remodeling Control Therapy and Anti-Remodeling Therapy by Implantable Cardiac Device", U.S. Appl. No. 10/850,341, filed May 20, 2004, 25 pgs.

No Authors Listed, "Heart rate variability: standards of measurement, physiological interpretation and clinical use. Task Force of the European Society of Cardiology and the North American Society of Pacing and Electrophysiology", *Circulation*, 93(5), (Mar. 1, 1996),1043-1065.

Scheiner, A., et al., "System and Method for Monitoring Autonomic Balance and Physical Activity", U.S. Appl. No. 10/695,430, filed Oct. 28, 2003, 20 pgs.

Koning, M M., "Rapid ventricular pacing produces myocardial protection by nonischemic activation of KATP+ channels", *Circulation*, 93(1), (Jan. 1, 1996),178-186.

Murry, C. E., "Preconditioning with ischemia: a delay of lethal cell injury in ischemic myocardium", *Circulation*, 74(5), (1986),1124-1136.

* cited by examiner

DEMAND-BASED CARDIAC FUNCTION THERAPY

FIELD OF THE INVENTION

This patent application pertains to methods and apparatus for the treatment of cardiac disease. In particular, it relates to methods and apparatus for improving cardiac function with electro-stimulatory therapy.

BACKGROUND

Implantable cardiac devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices may also be used to treat cardiac rhythms that are too fast, with either anti-tachycardia pacing or the delivery of electrical shocks to terminate atrial or ventricular fibrillation.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection an intrinsic atrial contraction.

Cardiac pacing therapy, if delivered synchronously, is demand-based. That is, pacing pulses are delivered only when the heart's intrinsic rhythm fails to maintain an adequate heart rate. Cardiac electro-stimulation delivered for purposes other than to enforce a minimum rate, however, is currently delivered in a more or less constant manner without regard for changes in the patient's condition.

SUMMARY

The present invention relates to a method and device for delivering cardiac function therapy on a demand basis. In accordance with the invention, an implantable device for delivering cardiac function therapy is programmed to suspend such therapy at periodic intervals or upon command from an external programmer. Measurements related to hemodynamic performance are then taken using one or more sensing modalities incorporated into the device. Based upon these measurements, the device uses a decision algorithm to determine whether further delivery of the cardiac function therapy is warranted.

DETAILED DESCRIPTION

Figure 1:
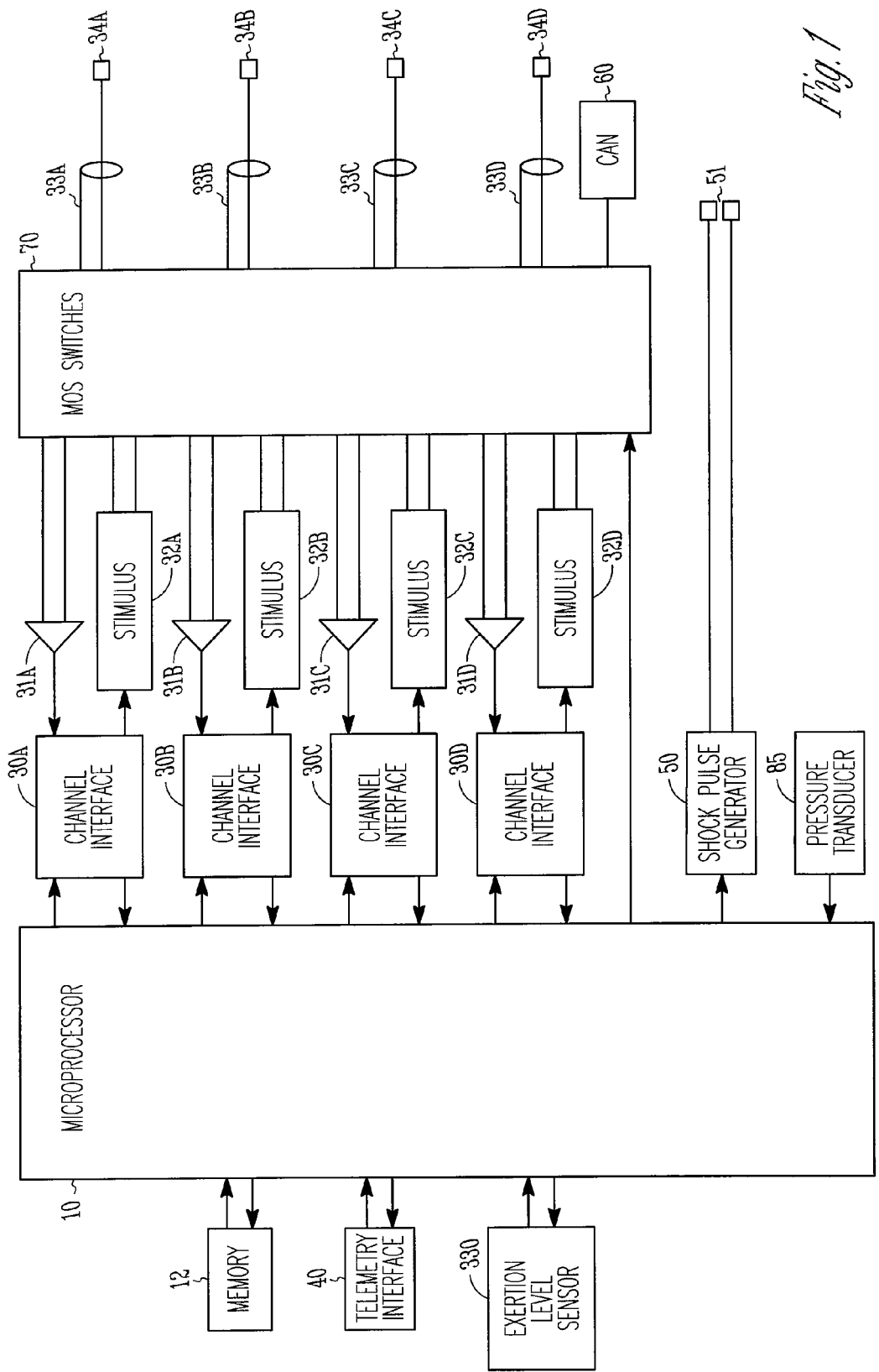
FIG. 1 is a system diagram of a cardiac device configured for multi-site stimulation and sensing.

As noted above, most current cardiac pacing devices are demand based, that is, any pacing mode or pacemaker that delivers an output pulse only when the intrinsic rate is less than the programmed base rate. Thus, a demand interval specifies the time period between two consecutive paced events in the same chamber without an intervening sensed event. As described below, implantable devices for delivering cardiac function therapies may be prescribed for post-MI patients or heart failure patients in order to boost cardiac output and/or to reverse cardiac remodeling. In such cases, the cardiac function therapy delivery can be made available on a demand basis in accordance with the present invention.

1. Cardiac Function Therapy

One example of electro-stimulatory therapy for the purpose of improving cardiac function is CRT. In ventricular resynchronization therapy, the ventricles are paced at more than one site in order to affect a spread of excitation that results in a more coordinated contraction and thereby overcome interventricular or intraventricular conduction defects. Biventricular pacing is one example of resynchronization therapy in which both ventricles are paced in order to synchronize their respective contractions. Resynchronization therapy may also involve multi-site pacing applied to only one chamber. For example, a ventricle may be paced at multiple sites with excitatory stimulation pulses in order to produce multiple waves of depolarization that emanate from the pacing sites. This may produce a more coordinated contraction of the ventricle and thereby compensate for intraventricular conduction defects that may exist.

Another type of cardiac function therapy is stress reduction pacing which involves altering the coordination of ventricular contractions with multi-site pacing in order to change the distribution of wall stress experienced by the ventricle during the cardiac pumping cycle. The degree to which a heart muscle fiber is stretched before it contracts is termed the preload. The maximum tension and velocity of shortening of a muscle fiber increases with increasing preload. The increase in contractile response of the heart with increasing preload is known as the Frank-Starling principle. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region that contracts later than other regions is subjected to both an increased preload and afterload. This situation is created frequently by the ventricular conduction delays associated with heart failure and ventricular dysfunction. The heart's initial physiological response to the uneven stress resulting from an increased preload and afterload is compensatory hypertrophy in those later contracting regions of the myocardium. In the later stages of remodeling, the regions may undergo atrophic changes with wall thinning due to the increased stress. The parts of the myocardium that contract earlier in the cycle, on the other hand, are subjected to less stress and are less likely to undergo hypertrophic remodeling. This phenomena may be used to effect reversal of remodeling by pacing one or more sites in a ventricle (or an atrium) with one or more excitatory stimulation pulses during a cardiac cycle with a specified pulse output sequence. The pace or paces are delivered in a manner that excites a previously stressed and remodeled region of the myocardium earlier during systole so that it experiences less afterload and preload. This pre-excitation of the remodeled region relative to other regions unloads the region from mechanical stress and allows reversal of remodeling to occur.

2. Hardware Platform

An implantable cardiac device is typically placed subcutaneously or submuscularly in a patient's chest with leads threaded intravenously into the heart to connect the device to electrodes used for sensing and stimulation. Leads may also be positioned on the epicardium by various means. A programmable electronic controller causes the stimulus pulses to be output in response to lapsed time intervals and sensed electrical activity (i.e., intrinsic heart beats not as a result of a stimulus pulse). The device senses intrinsic cardiac electrical activity by means of internal electrodes disposed near the chamber to be sensed. A depolarization wave associated with an intrinsic contraction of the atria or ventricles that is detected by the device is referred to as an atrial sense or ventricular sense, respectively. In order to cause such a contraction in the absence of an intrinsic beat, a stimulus pulse (a.k.a. a pace or pacing pulse when delivered in order to enforce a certain rhythm) with energy above a certain threshold is delivered to the chamber.

FIG. 1 shows a system diagram of a microprocessor-based cardiac device suitable for practicing the present invention. The device is equipped with multiple sensing and pacing channels which may be physically configured to sense and/or pace multiple sites in the atria or the ventricles. The device shown in FIG. 1 can be configured for cardiac resynchronization pacing of the atria or ventricles and/or for myocardial stress reduction pacing such that one or more cardiac sites are sensed and/or paced in a manner that pre-excites at least one region of the myocardium. The multiple sensing/stimulation channels may be configured, for example, with one atrial and two ventricular sensing/stimulation channels for delivering biventricular resynchronization therapy, with the atrial sensing/stimulation channel used to deliver biventricular resynchronization therapy in an atrial tracking mode as well as to pace the atria if required. The controller 10 of the pacemaker is a microprocessor which communicates with a memory 12 via a bidirectional data bus. The memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor.

Shown in the figure are four exemplary sensing and pacing channels designated "a" through "d" comprising bipolar leads with ring electrodes 33a-d and tip electrodes 34a-d, sensing amplifiers 31a-d, pulse generators 32a-d, and channel interfaces 30a-d. Each channel thus includes a pacing channel made up of the pulse generator connected to the electrode and a sensing channel made up of the sense amplifier connected to the electrode. The channel interfaces 30a-d communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The electrodes of each bipolar lead are connected via conductors within the lead to a MOS switching network 70 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing or can 60 serving as a ground electrode. As explained below, one way in which the device may alter the spatial distribution of pacing is to switch from unipolar to bipolar pacing (or vice-versa) or to interchange which electrodes of a bipolar lead are the cathode and anode during bipolar pacing. A shock pulse generator 50 is also interfaced to the controller for delivering a defibrillation shock via a pair of shock electrodes 51 to the atria or ventricles upon detection of a shockable tachyarrhythmia.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. An exertion level sensor 330 (e.g., an accelerometer, a minute ventilation sensor, or other sensor that measures a parameter related to metabolic demand) enables the controller to adapt the pacing rate in accordance with changes in the patient's physical activity. A telemetry interface 40 is also provided which enables the controller to communicate with an external programmer.

In one embodiment, the exertion level sensor is a minute ventilation sensor which includes an exciter and an impedance measuring circuit. The exciter supplies excitation current of a specified amplitude (e.g., as a pulse waveform with constant amplitude) to excitation electrodes that are disposed in the thorax. Voltage sense electrodes are disposed in a selected region of the thorax so that the potential difference between the electrodes while excitation current is supplied is representative of the transthoracic impedance between the voltage sense electrodes. The conductive housing or can may be used as one of the voltage sense electrodes. The impedance measuring circuitry processes the voltage sense signal from the voltage sense electrodes to derive the impedance signal. Further processing of the impedance signal allows the derivation of signal representing respiratory activity and/or cardiac blood volume, depending upon the location the voltage sense electrodes in the thorax. (See, e.g., U.S. Pat. Nos. 5,190,035 and 6,161,042, assigned to the assignee of the present invention and hereby incorporated by reference.) If the impedance signal is filtered to remove the respiratory component, the result is a signal that is representative of blood volume in the heart at any point in time, thus allowing the computation of stroke volume and, when combined with heart rate, computation of cardiac output.

The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. Cardiac function therapy, whether for the purpose of cardiac resynchronization or for reversal of remodeling, is most conveniently delivered in conjunction with a bradycardia pacing mode where, for example, multiple excitatory stimulation pulses are delivered to multiple sites during a cardiac cycle in order to both pace the heart in accordance with a bradycardia mode and provide pre-excitation of selected sites.

A particular pacing mode for delivering cardiac function therapy, whether for stress reduction or resynchronization, includes a defined pulse output configuration and pulse output sequence, where the pulse output configuration specifies a specific subset of the available electrodes to be used for delivering pacing pulses and the pulse output sequence specifies the timing relations between the pulses. The pulse output configuration is defined by the controller selecting particular pacing channels for use in outputting pacing pulses and by selecting particular electrodes for use by the channel with switch matrix 70. The pulse output configuration and sequence which optimally effects reverse remodeling by selectively reducing myocardial wall stress may or may not be the optimum pulse output configuration and sequence for maximizing hemodynamic performance by resynchronizing ventricular contractions. For example, a more hemodynamically effective contraction may be obtained by exciting all areas of the myocardium simultaneously, which may not effectively promote reversal of the hypertrophy or remodeling.

3. Demand-based Cardiac Function Therapy

In order to deliver cardiac function therapy on a demand basis, the controller of an implantable cardiac device is programmed to suspend delivery of the cardiac function therapy and assess the patient's cardiac function by means of one or more sensing modalities. A decision algorithm is then employed to determine subsequent therapy. In one embodiment, a binary decision algorithm either continues or indefinitely suspends the cardiac function therapy based upon the cardiac function assessment. For example, stress reduction therapy may be employed in a heart failure or post-MI patient to effect reversal of cardiac remodeling. If the cardiac function assessment indicates that the patient's condition is unchanged or has deteriorated, the device resumes the stress reduction therapy. If the patient's cardiac function has improved sufficiently, on the other hand, the device indefinitely terminates the therapy. Delivery of cardiac resynchronization therapy may similarly be continued or terminated based upon the cardiac function assessment. After termination of cardiac function therapy, the device may continue to monitor the patient's cardiac function, periodically or otherwise, so that therapy can be resumed if needed. In addition, the device may periodically switch on therapies and see whether patient conditions have evolved gradually and therapy delivery is warranted again.

In another embodiment, the delivery of cardiac function therapy is modified in accordance with the assessment of cardiac function. The cardiac function therapy may be modified by changing the pulse output configuration, the pulse output sequence, and/or various pacing parameters. For example, the device may change from a pulse output configuration and sequence considered optimal for reversal of remodeling to one considered optimal for resynchronization pacing or vice-versa as a result of the cardiac function assessment. In another example, pacing parameters such as the length of one or more escape intervals, a biventricular offset interval for biventricular pacing, or an AV delay interval for atrial tracking or AV sequential pacing are changed in accordance with the cardiac function assessment.

a. Assessment of Cardiac Function

One means by which cardiac function may be assessed is by measuring cardiac output and comparing it with the patient's measured exertion level. As described earlier, cardiac output may be measured by an impedance technique in which transthoracic impedance is measured and used compute stroke volume. The stroke volume integrated over time (or averaged and multiplied by heart rate) gives the patient's cardiac output. A look-up table or linear function may be used to compute what cardiac output is considered adequate for a given exertion level. Based upon these measurements, the device may then decide whether cardiac function therapy is warranted.

Another means for assessing cardiac function is by determining the autonomic balance of the patient. It is well-known that an increase in the activity of the sympathetic nervous system may be indicative of metabolic stress and the need for increased cardiac output. One means by which increased sympathetic activity may be detected is via spectral analysis of heart rate variability. Heart rate variability refers to the variability of the time intervals between successive heart beats during a sinus rhythm and is primarily due to the interaction between the sympathetic and parasympathetic arms of the autonomic nervous system. Spectral analysis of heart rate variability involves decomposing a signal representing successive beat-to-beat intervals into separate components representing the amplitude of the signal at different oscillation frequencies. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity. An LF/HF ratio which exceeds a specified threshold value may be taken as an indicator that cardiac function is not adequate.

A cardiac rhythm management device can be programmed to determine the LF/HF ratio by analyzing data received from its ventricular sensing channels. The intervals between successive ventricular senses, referred to as RR intervals, can be measured and collected for a period of time or a specified number of beats. In order to derive a signal representing heart rate variability during a sinus rhythm, ectopic ventricular beats (i.e., premature ventricular contractions or PVCs) can be detected by monitoring whether a P wave precedes each R wave, with the RR intervals before and after the PVC changed to an interpolated or otherwise filtered value. The resulting series of RR interval values is then stored as a discrete signal. The signal can be used directly as indexed by heartbeat such that each value of the signal represents an RR interval for a particular heartbeat. Preferably, however, the signal is resampled at a specified sampling frequency in order to equalize the time intervals between signal values and thus convert the signal into a discrete time signal, where the sampling frequency is selected to meet the Nyquist criterion with respect to the frequencies of interest. In any case, the RR interval signal can then be analyzed to determine its energies in the high and low frequency bands as described above.

Figure 2:
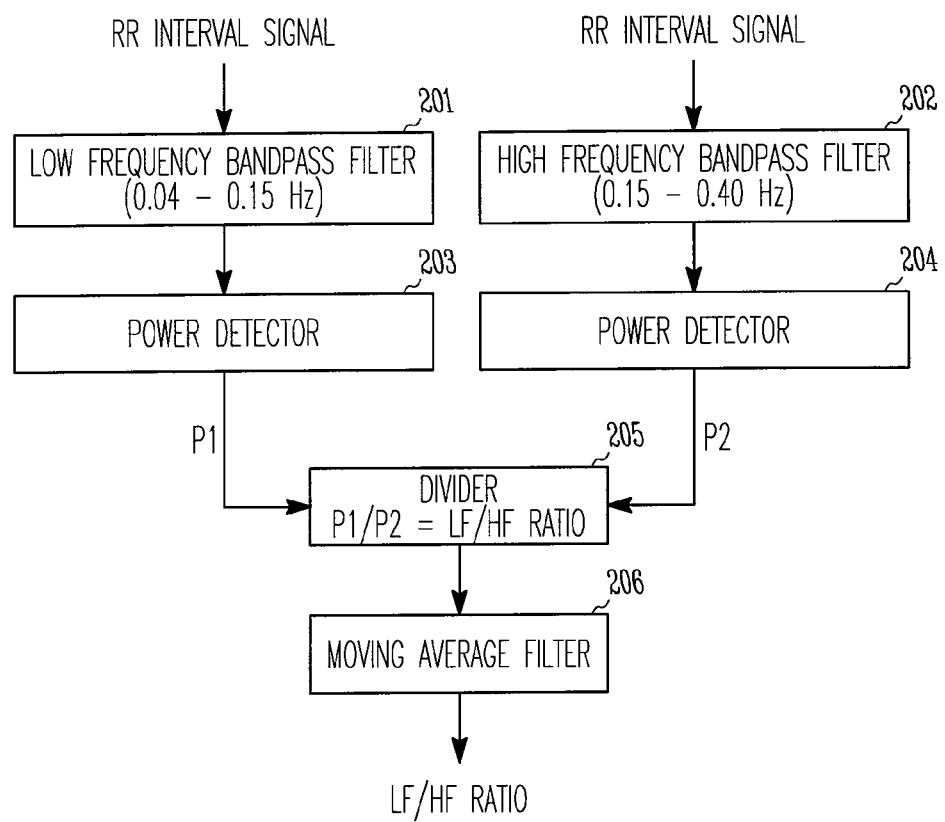
FIG. 2 is a block diagram of exemplary components for computing the LF/HF ratio.

Spectral analysis of an RR interval signal can be performed directly in the frequency domain using discrete Fourier transform or autoregression techniques. Frequency domain analysis is computationally intensive, however, and may not be practical in an implantable device. A time-domain technique for determining the high and low frequency components of the signal is therefore preferably used. FIG. 2 illustrates the functional components of an exemplary system for doing this that can be implemented as code executed by the controller and/or dedicated hardware components. The RR interval signal obtained as described above is input to both a low band digital filter 201 and a high band digital filter 202. The low band filter 201 is a bandpass filter with a passband corresponding to the LF band (e.g., 0.04 to 0.15 Hz), while the high band filter 202 is a bandpass filter with a passband corresponding to the HF band (e.g., 0.15 to 0.40 Hz). The outputs of filters 201 and 202 are then input to power detectors 203 and 204, respectively, in order to derive signals proportional to the power of the RR interval signal in each of the LF and HF bands. Power detection may be performed, for example, by squaring the amplitude of the signal and integrating over a specified average time. The output of power detector 203 is thus a signal P1 that represents the power of the RR interval signal in the LF band, and the output of power detector 204 is a signal P2 representing the power in the HF band. The signals P1 and P2 are next input to a divider 205 that computes the quantity S1/S2 which equals the LF/HF ratio. The LF/HF ratio is then input to a moving average filter 206 that computes an average value for the ratio over a specified period (e.g., 5 minutes). An updated LF/HF ratio may be computed in this manner on a beat-to-beat basis.

In the above description, heart rate variability was derived from the RR interval signal during normal sinus rhythm. It should also be appreciated that, if normal sinus rhythm is present, the RR interval is equivalent to the interval between successive atrial senses. As used herein, therefore, the term RR interval should be regarded as the interval between heart beats during sinus rhythm whether the beats are atrial or ventricular. Also, as an alternative to time-domain filtering, a statistical method of estimating the LF/HF ratio may be employed as described in U.S. patent application Ser. No. 10/436,876 filed May 12, 2003 and herein incorporated by reference.

Other means of assessing cardiac function may also be employed to deliver demand-based cardiac function therapy. The impedance technique for measuring cardiac output discussed above may also be used to measure ventricular volumes at various stages of the cardiac cycle such as end-diastolic and end-systolic volumes and used to compute parameters reflective of cardiac function such as ejection fraction. The implantable device may also be equipped with other sensing modalities such as a pressure transducer 85 shown in FIG. 1. Such a pressure transducer may be attached to an intravascular lead and be appropriately disposed for measuring diastolic filling pressures and/or systolic pulse pressures.

b. Exemplary Algorithm

Figure 3:
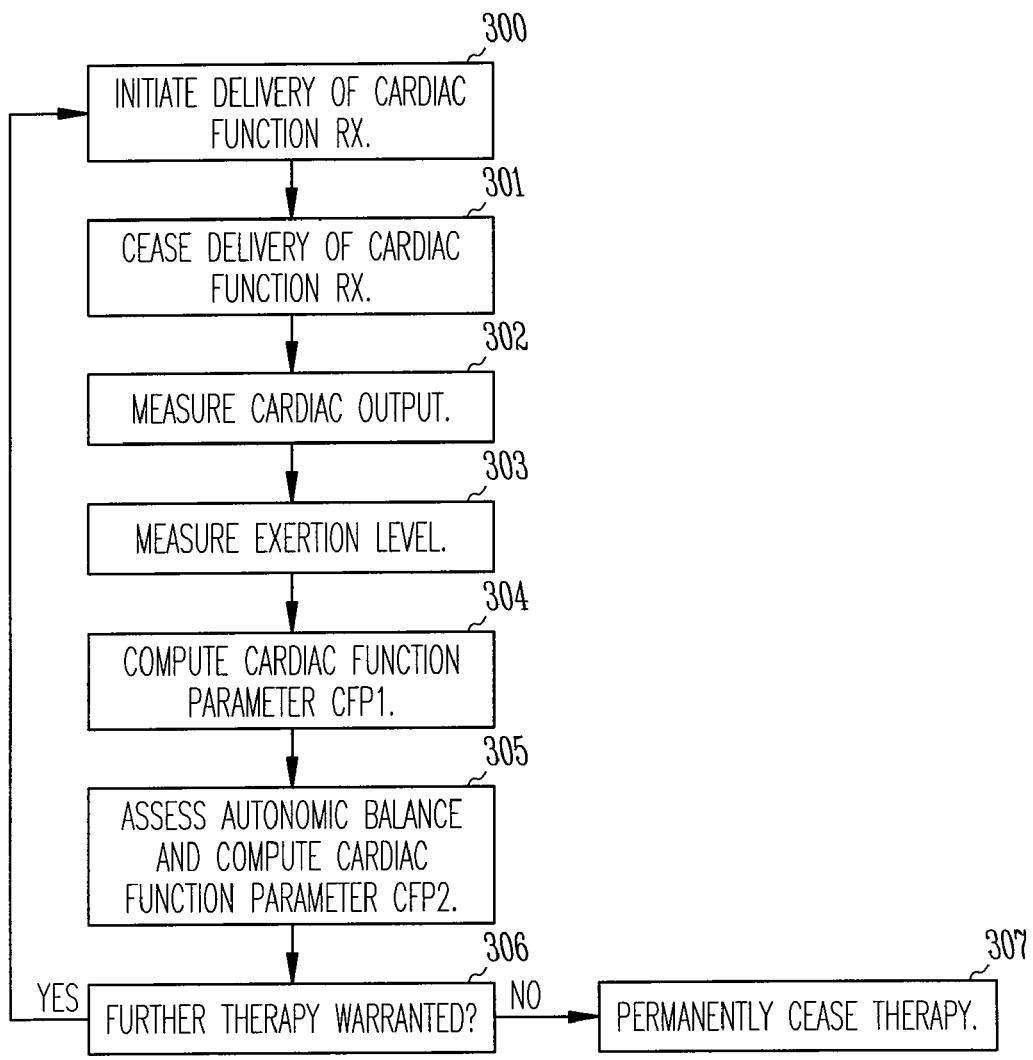
FIG. 3 illustrates an exemplary algorithm for implementing the invention.

FIG. 3 illustrates an exemplary algorithm for demand-based cardiac function therapy as could be implemented by appropriate programming of the implantable device controller. Starting at step 300, the device initiates cardiac function therapy such as stress reduction pacing or resynchronization pacing with a specified pacing mode and using a specified pulse output configuration and pulse output sequence. At step 301, either at periodic intervals or upon command from an external programmer via the telemetry interface, the device suspends further delivery of cardiac function therapy. At step 302, the device next begins an assessment of the patient's cardiac function using one or more sensing modalities. In this embodiment, the device computes cardiac output by measurement of the heart rate and cardiac stroke volume via the intra-thoracic impedance method. The patient's exertion level 303 (e.g., either activity level or minute ventilation) is then measured and compared with the measured cardiac output measurement at step 303 to determine whether the patient's cardiac output is adequate for that particular exertion level. Based upon this comparison a first cardiac function parameter CFP1 may be computed at step 304 which, if below a specified threshold level, indicates inadequate cardiac function. Next, the patient's autonomic balance is assessed at step 305, and a second cardiac function parameter CFP2 is computed which is indicative of the extent of metabolic stress experienced by the patient. This parameter can also be compared with a specified threshold value for decision-making purposes. Based upon the computed cardiac function parameters CFP1 and CFP2, the device at step 306 decides whether the patient's cardiac function is inadequate. If so, the device continues cardiac function therapy by returning to step 300. If the computed cardiac function parameters indicate that the patient's cardiac function has improved to a sufficient extent, on the other hand, the device indefinitely suspends further delivery of cardiac function therapy at step 307.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method, comprising:
implanting a cardiac pacing device having a plurality of pacing channels in a patient so as to allow paces to be delivered to a plurality of ventricular sites;
configuring the cardiac pacing device to deliver cardiac function therapy that effects reversal of ventricular remodeling by delivering pacing pulses to one or more stressed or hypertrophied ventricular regions in a manner that pre-excites those region(s) relative to other ventricular regions;
measuring the cardiac output of the patient;
measuring the exertion level of the patient;
configuring the cardiac pacing device to assess the patient's cardiac function by comparing the measured cardiac output with the measured exertion level and computing a cardiac function parameter indicative as to whether the patient's cardiac output is adequate for the measured exertion level; and
configuring the cardiac pacing device to temporarily suspend delivery of cardiac function therapy, assess the patient's cardiac function while no cardiac function therapy is being delivered by comparing the cardiac function parameter to a threshold value, continuing delivery of cardiac function therapy if the patient's cardiac function is determined to be inadequate, and ceasing delivery of cardiac function therapy if the patient's cardiac function is determined to have improved to a specified extent.

2. The method of claim 1 further comprising measuring cardiac blood volume and wherein the cardiac function parameter is further computed based upon an ejection fraction derived from measurements of end-diastolic and end-systolic volumes.

3. The method of claim 1 further comprising measuring diastolic filling pressures and systolic pulse pressures and wherein the cardiac function parameter is further computed based upon the measured diastolic filling pressures and systolic pulse pressures.

4. The method of claim 1 wherein the cardiac output is measured by measuring a trans-thoracic impedance and heart rate.

5. The method of claim 1 wherein the exertion level measurement is selected from an activity level measurement and a minute ventilation measurement.

6. The method of claim 1 wherein the cardiac function assessment includes an assessment of the patient's autonomic balance by measuring the patient's heart rate variability.

7. The method of claim 6 further comprising:
measuring and collecting time intervals between successive chamber senses and storing the collected intervals as a discrete RR interval signal, filtering the RR interval signal into defined high and low frequency bands, and determining the signal power of the RR interval signal in each of the low and high frequency bands, referred to LF and HF, respectively; and,
computing an LF/HF ratio and assessing cardiac function by comparing the LF/HF ratio to a specified ratio threshold value.

8. The method of claim 1 wherein the suspension of cardiac function therapy and assessment of the patient's cardiac function are performed upon a command from an external programmer.

9. The method of claim 1 wherein the suspension of cardiac function therapy and assessment of the patient's cardiac function are performed at periodic intervals.

* * * * *